United States Patent [19]

Baumann et al.

[11] Patent Number: 5,318,945
[45] Date of Patent: Jun. 7, 1994

[54] THIOCARBOXYLIC ACID DERIVATIVES

[75] Inventors: Ernst Baumann, Speyer; Thomas Saupe, Sandhausen; Joachim Rheinheimer; Uwe J. Vogelbacher, both of Ludwigshafen; Matthias Bratz, Speyer; Norbert Meyer, Ladenburg; Matthias Gerber, Mutterstadt; Karl-Otto Westphalen, Speyer; Uwe Kardorff, Mannheim; Andreas Landis, Limburgerhof; Helmut Walter, Obrigheim, all of Fed. Rep. of Germany

[73] Assignee: BASF Aktiengesellschaft, Ludwigshafen, Fed. Rep. of Germany

[21] Appl. No.: 994,254

[22] Filed: Dec. 21, 1992

[30] Foreign Application Priority Data

Jan. 24, 1992 [DE] Fed. Rep. of Germany ....... 4201875

[51] Int. Cl.$^5$ ................ C07D 239/52; C07D 239/34; C07D 239/60; A01N 43/54
[52] U.S. Cl. .................................... 504/243; 504/242; 504/241; 504/240; 544/253; 544/278; 544/301; 544/302; 544/311; 544/312; 544/313; 544/314; 544/316; 544/318
[58] Field of Search ............... 504/240, 241, 242, 243; 544/278, 300, 310, 314, 253, 312

[56] References Cited

U.S. PATENT DOCUMENTS

| 4,968,340 | 11/1990 | Kaku et al. | 71/92 |
| 5,087,289 | 2/1992 | Kaku et al. | 71/93 |
| 5,139,563 | 8/1992 | Astles et al. | 71/92 |

FOREIGN PATENT DOCUMENTS 0409368 7/1990 European Pat. Off.

OTHER PUBLICATIONS

Harada et al., Chemical Abstracts, vol. 118, entry 213114q (1992).
Harada et al., Chemical Abstracts, vol. 117, entry 48615r (1992).
Sasaki et al., Chemical Abstracts, vol. 115, entry 71639u (1991).
Astles et al., Chemical Abstracts, vol. 114, entry 185569f (1991).
Crabtree, Chemical Abstracts, vol. 73, entry 57176 (1970).

Primary Examiner—John M. Ford
Attorney, Agent, or Firm—Keil & Weinkauf

[57] ABSTRACT

Thiocarboxylic acid derivatives useful as herbicides or plant growth regulators are of the general formula I

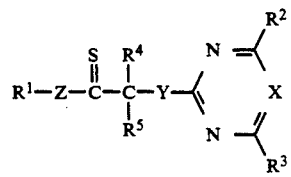

where
$R^1$ is unsubstituted or substituted alkyl, unsubstituted or substituted cycloalkyl or cycloalkenyl, unsubstituted or substituted alkenyl or alkynyl or unsubstituted or substituted phenyl;
$R^2$ is halogen, alkyl, haloalkyl, alkoxy, haloalkoxy or alkylthio;
X is nitrogen or $CR^6$, where $R^6$ is hydrogen or, together with $R^3$, forms a $C_3$- or $C_4$-alkylene chain or $C_3$- or $C_4$-alkenylene chain in which a methylene group is replaced with oxygen;
$R^3$ is halogen, alkyl, haloalkyl, alkoxy, haloalkoxy or alkylthio or $R^3$ is bonded to $R^6$ as stated above to give a 5-membered or 6-membered ring;
$R^4$ is unsubstituted or substituted alkyl, unsubstituted or substituted alkenyl or alkynyl, an unsubstituted or substituted 5-membered or 6-membered heteroaromatic structure containing from one to three nitrogen atoms and/or one sulfur or oxygen atom, or unsubstituted or substituted phenyl or naphthyl;
$R^4$ and $R^5$ together with the adjacent carbon atom form a 3-membered to 6-membered ring which may contain an oxygen or sulfur atom and may be substituted;
$R^5$ is hydrogen, alkyl, haloalkyl, alkoxy, haloalkoxy, or alkylthio;
and Y and Z are each oxygen or sulfur.

9 Claims, No Drawings

THIOCARBOXYLIC ACID DERIVATIVES

The present invention relates to thiocarboxylic acid derivatives of the general formula I

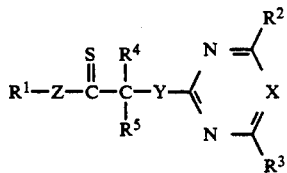

where $R^1$ is $C_1$–$C_{10}$-alkyl which may carry from one to five halogen atoms and/or one of the following radicals: $C_1$–$C_4$-alkoxy, $C_1$–$C_4$-alkylthio, cyano, $C_1$–$C_8$-alkylcarbonyl, $C_1$–$C_8$-alkoxy-carbonyl, $C_3$–$C_{12}$-cycloalkyl, phenyl, phenoxy or phenylcarbonyl, where the phenyl radicals in turn may carry from one to five halogen atoms and/or from one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio; $C_1$–$C_{10}$-alkyl which may carry from one to five halogen atoms and carries one of the following radicals: a five-membered heteroaromatic structure containing from one to three nitrogen atoms and/or one sulfur or oxygen atom, which may carry from one to four halogen atoms and/or one or two of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

$C_2$–$C_6$-alkyl which carries one of the following radicals in the 2-position: $C_1$–$C_6$-alkoximino, $C_3$–$C_6$-alkenyloximino, $C_3$–$C_6$-haloalkenyloximino or benzyloximino; $C_3$–$C_{12}$-cycloalkyl or $C_3$–$C_{12}$-cycloalkenyl which may carry from one to five halogen atoms and/or one of the following radicals: $C_1$–$C_4$-alkyl, $C_1$–$C_4$-alkoxy, $C_1$–$C_4$-alkylthio, cyano, $C_1$–$C_8$-alkylcarbonyl, $C_1$–$C_8$-alkoxycarbonyl, phenyl, phenoxy or phenylcarbonyl, where the phenyl radicals in turn may carry from one to five halogen atoms and/or from one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

$C_3$–$C_6$-alkenyl or $C_3$–$C_6$-alkynyl which may carry from one to five halogen atoms and/or one of the following radicals: $C_1$–$C_4$-alkoxy, $C_1$–$C_4$-alkylthio, cyano, $C_1$–$C_8$-alkylcarbonyl, $C_1$–$C_8$-alkoxycarbonyl, phenyl, phenoxy or phenylcarbonyl, where the phenyl radicals in turn may carry from one to five halogen atoms and/or from one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

phenyl which is unsubstituted or monosubstituted to trisubstituted by $C_1$–$C_4$-alkyl or $C_1$–$C_4$-alkoxy or monosubstituted to pentasubstituted by halogen;

$R^2$ is halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

X is nitrogen or $CR^6$, where $R^6$ is hydrogen or, together with $R^3$, forms a 3-membered or 4-membered alkylene or alkenylene chain, in each of which a methylene group is replaced with oxygen and each of which may be substituted by $C_1$–$C_4$-alkyl, phenyl, $C_1$–$C_4$-alkoxy, or $C_1$–$C_4$-alkoxycarbonyl;

$R^3$ halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio or $R^3$ is bonded to $R^6$ as stated above to form a 5-membered or 6-membered ring;

$R^4$ is $C_1$–$C_{10}$-alkyl which may carry from one to five halogen atoms and/or one of the following radicals: $C_1$–$C_4$-alkoxy, $C_1$–$C_4$-alkylthio, cyano, $C_1$–$C_8$-alkylcarbonyl, $C_1$–$C_8$-alkoxycarbonyl, phenyl, phenoxy or phenylcarbonyl, where the phenyl radicals in turn may carry from one to five halogen atoms and/or from one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

$C_1$–$C_{10}$-alkyl which may carry from one to five halogen atoms and carries one of the following radicals: a five-membered heteroaromatic structure containing from one to three nitrogen atoms and/or one sulfur or oxygen atom, which may carry from one to four halogen atoms and/or one or two of the following radicals: $C_1$–$C_4$-alkyl, $C_1$–$C_4$-haloalkyl, $C_1$–$C_4$-alkoxy, $C_1$–$C_4$-haloalkoxyl, $C_1$–$C_4$-alkylthio and/or phenyl;

$C_3$–$C_{12}$-cycloalkyl or $C_3$–$C_{12}$-cycloalkenyl, each of which may contain an oxygen or sulfur atom and may carry from one to five halogen atoms and/or one of the following radicals: $C_1$–$C_4$-alkyl, $C_1$–$C_4$-alkoxy, $C_1$–$C_4$-alkylthio, cyano, $C_1$–$C_8$-alkylcarbonyl, $C_1$–$C_8$-alkoxycarbonyl, phenyl, phenoxy or phenylcarbonyl, where the phenyl radicals in turn may carry from one to five halogen atoms and/or from one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

$C_3$–$C_6$-alkenyl or $C_3$–$C_6$-alkynyl, each of which may carry from one to five halogen atoms and/or one of the following radicals: $C_1$–$C_4$-alkyl, $C_1$–$C_4$-alkoxy, $C_1$–$C_4$-alkylthio, cyano, $C_1$–$C_8$-alkylcarbonyl, $C_1$–$C_8$-alkoxycarbonyl, phenyl, phenoxy or phenylcarbonyl, where the phenyl radicals in turn may carry from one to five halogen atoms and/or from one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

a five-membered or six-membered heteroaromatic structure containing from one to three nitrogen atoms and/or one sulfur or oxygen atom, which may carry from one to four halogen atoms and/or one or two of the following radicals: $C_1$–$C_4$alkyl, $C_1$–$C_4$-haloalkyl, $C_1$–$C_4$-alkoxy, $C_1$–$C_4$-haloalkoxy, $C_1$–$C_4$-alkylthio, phenyl, phenoxy or phenylcarbonyl, where the phenyl radicals in turn may carry from one to five halogen atoms and/or from one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

phenyl or naphthyl which may carry from one to five halogen atoms and/or one or two of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

$R^4$ and $R^5$ together with the adjacent carbon atom form a 3-membered to 6-membered ring which may contain an oxygen or sulfur atom and may carry from one to three of the following radicals: $C_1$–$C_4$-alkyl, $C_1$–$C_4$-haloalky, $C_1$–$C_4$-alkoxy, $C_1$–$C_4$-haloalkoxy and/or $C_1$–$C_4$-alkylthio;

$R^5$ is hydrogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, or $R^5$ is bonded to $R^4$ as stated above to form a 3-membered to 6-membered ring, and Y and Z are each oxygen or sulfur.

The formula I embraces both the racemic products and the optically active derivatives in the case of non-identical radicals $R^4$ and $R^5$ (R-configuration, S-configuration).

The literature (EP-A 347 811, EP-A 400 741, EP-A 409 368) describes herbicidal α-pyrimidinyloxy(thio)-carboxylic acid derivatives. However, the action and selectivity of these compounds are not always satisfactory.

It is an object of the present invention to provide novel carboxylic acid derivatives having improved herbicidal and plant growth-regulating properties.

We have found that this object is achieved and that the thiocarboxylic acid derivatives defined at the outset and of the general formula I have excellent herbicidal and plant growth-regulating properties.

For the preparation of the novel compounds, cyanohydrine II, which are obtained in a generally known manner, for example as described in J. March, Advanced Organic Chemistry, 2nd Ed., 1983, page 873, from the corresponding ketones or aldehydes $R^4COR^5$, are used as starting materials. These cyanohydrins are reacted with roughly equimolar amounts of pyrimidine or triazine derivatives of the formula III, where W is a nucleofugic group, for example chlorine or $R^7SO_2$, such as methylsulfonyl or phenylsulfonyl, with the aid of an organic or inorganic base in an inert organic solvent to give nitriles of the general formula IV.

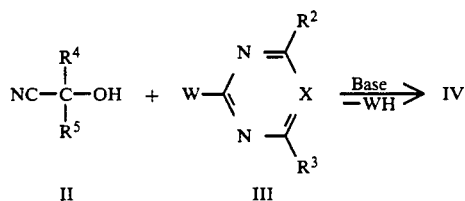

The heteroaromatics III are generally known, for example from the prior art cited at the outset. Compounds III in which X is $CR^6$ and $R^6$ together with $R^3$ forms a 5-membered or 6-membered, unsaturated or monosaturated ring containing an oxygen atom are obtained by oxidizing a corresponding 2-alkylthio-5,6-dihydrofuran[2,3]-pyrimidine (cf. Collect. Czech. Chem. Commun. 32 (1967), 1582)

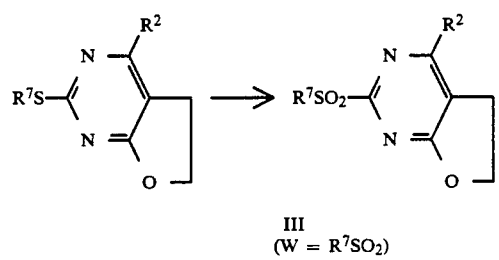

with an oxidizing agent, for example chlorine in water or hydrogen peroxide in glacial acetic acid, under mild conditions.

The preparation of fused pyrimidines is furthermore described, for example, in

Bull. Soc. Chim. France (1969), 4344
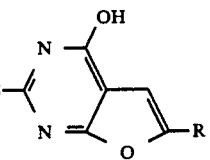

Arch. Pharmazie (Weinheim) 311 (1978), 1019
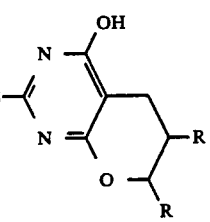

Lipids 21 (1986), 537
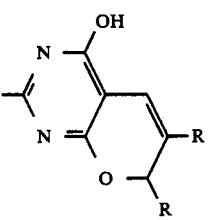

Chem. Ber. 103 (1970), 1250
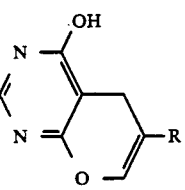

In formula III, $R^7SO_2$ is a conventional nucleofugic leaving group, for example arylsulfonyl, such as phenylsulfonyl or substituted phenylsulfonyl, suitable substituents being one or more, for example from 1 to 3, low molecular weight alkyl or alkoxy radicals, such as $C_1$–$C_4$-alkyl or alkoxy, or halogen, eg. chlorine, fluorine or bromine; or alkylsulfonyl, such as $C_1$–$C_4$-alkylsulfonyl, eg. methylsulfonyl.

Suitable bases are alkali metal or alkaline earth metal hydrides, such as NaH or $CaH_2$, alkali metal hydroxides, such as NaOH or KOH, alkali metal alcoholates, such as potassium tert-butylate, alkali metal carbonates, such as $Na_2CO_3$ or $K_2CO_3$, alkali metal amides, such as $NaNH_2$ or lithium diisopropylamide, or tertiary amines. When an inorganic base is used, it is possible to add a phase transfer catalyst if the latter increases the conversion.

By treatment with excess hydrogen sulfide in an inert solvent, the nitriles IV are converted into the corresponding thioamides V

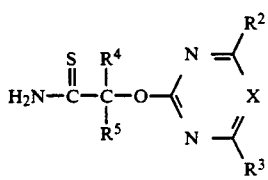

which are reacted which a compound VI $R^1A$  VI where $R^1$ has the abovementioned meanings and A is a nucleofugic leaving group, for example halogen, alkylsulfate or dialkyloxonium tetrafluoroborate, in an inert solvent, and the product is then treated with excess hydrogen sulfide to give the desired compounds of the formula I where Y is O.

Usually, a small excess of VI, based on the thioamides V, for example from 1.05 to 1.2 equivalents of VI, is used.

Alternatively, the novel compounds may be obtained by reacting the carboxylic acid derivatives which are disclosed in, for example, EP-A 347 811, EP-A 400 741 or EP-A 409 368 and are of the formula VII

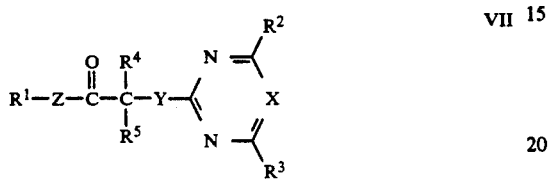

where the substituents have the abovementioned meanings, with Lawesson's reagent (Bull. Soc. Chim. Belg. 87 (1987), 293).

With regard to the biological activity, preferred thiocarboxylic acid derivatives I are those in which $R^1$ is $C_1$–$C_{10}$-alkyl, in particular $C_1$–$C_8$-alkyl, such as methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 2-methylhexyl, 3-methylhexyl, 4-methylhexyl, 5-methylhexyl, 1-ethylpentyl, 2-ethylpentyl, 1-propylbutyl or octyl, which may carry from one to five halogen atoms, such as fluorine, chlorine, bromine or iodine, in particular fluorine or chlorine, and/or one of the following radicals:

cyano, $C_1$–$C_4$-alkoxy, such as methoxy, ethoxy, propoxy, 1-methylethoxy, butoxy, 1-methylpropoxy, 2-methylpropoxy, 1,1-dimethylethoxy, in particular methoxy, ethoxy or 1-methylethoxy;

$C_1$–$C_4$-alkylthio, such as methylthio, ethylthio, propylthio, 1-methylethylthio, butylthio, 1-methylpropylthio, 2-methylpropylthio or 1,1-dimethylethylthio, in particular methylthio or ethylthio;

$C_1$–$C_8$-alkylcarbonyl, in particular methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl;

$C_1$–$C_8$-alkoxycarbonyl, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl, 1,1-dimethylethoxycarbonyl, n-pentyloxycarbonyl, 1-methylbutoxycarbonyl, 2-methylbutoxycarbonyl, 3-methylbutoxycarbonyl, 1,2-dimethylpropoxycarbonyl, 1,1-dimethylpropoxycarbonyl, 2,2-dimethylpropoxycarbonyl, 1-ethylpropoxycarbonyl, n-hexyloxycarbonyl, 1-methylpentyloxycarbonyl, 2-methylpentyloxycarbonyl, 3-methylpentyloxycarbonyl, 4-methylpentyloxycarbonyl, 1,2-dimethylbutoxycarbonyl, 1,3-dimethylbutoxycarbonyl, 2,3-dimethylbutoxycarbonyl, 1,1-dimethylbutoxycarbonyl, 2,2-dimethylbutoxycarbonyl, 3,3-dimethylbutoxycarbonyl, 1,1,2-trimethylpropoxycarbonyl, 1,2,2-trimethylpropoxycarbonyl, 1-ethylbutoxycarbonyl, 2-ethylbutoxycarbonyl, 1-ethyl-2-methylpropoxycarbonyl, n-heptyloxycarbonyl, 1-methylhexyloxycarbonyl, 2-methylhexyloxycarbonyl, 3-methylhexyloxycarbonyl, 4-methylhexyloxycarbonyl, 5-methylhexyloxycarbonyl, 1-ethylpentyloxycarbonyl, 2-ethylpentyloxycarbonyl, 1-propylbutoxycarbonyl or octyloxycarbonyl, in particular methoxycarbonyl, ethoxycarbonyl, 1-methylethoxycarbonyl or 1-methylpropoxycarbonyl;

$C_3$–$C_{12}$-cycloalkyl, in particular $C_3$–$C_6$-cycloalkyl, such as cyclopropyl, cyclobutyl, cyclopentyl or cyclohexyl;

phenyl, phenoxy or phenylcarbonyl, where the phenyl radicals in turn may carry from one to five halogen atoms as stated above and/or from one to three of the following radicals:

$C_1$–$C_4$-alkyl, such as methyl, ethyl, 1-propyl, 2-propyl, 2-methyl-2-propyl, 2-methyl-1-propyl, 1-butyl or 2-butyl;

$C_1$–$C_4$-haloalkyl, in particular $C_1$- or $C_2$-haloalkyl, for example fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl;

$C_{1-4}$-haloalkoxy, in particular $C_1$- or $C_2$-haloalkoxy, such as difluoromethoxy, trifluoromethoxy, chlorodifluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular trifluoromethoxy;

$C_1$–$C_4$-alkoxy, such as methoxy, ethoxy, propoxy, 1-methylethoxy, butoxy, 1-methylpropoxy, 2-methylpropoxy or 1,1-dimethylethoxy, in particular methoxy, ethoxy or 1-methylethoxy;

$C_1$–$C_4$-alkylthio, such as methylthio, ethylthio, propylthio, 1-methylethylthio, butylthio, 1-methylpropylthio, 2-methylpropylthio or 1,1-dimethylethylthio, in particular methylthio or ethylthio;

$R^1$ is furthermore $C_1$–$C_{10}$-alkyl, in particular $C_1$–$C_4$-alkyl as stated above, which may carry from one to five halogen atoms as stated above, preferably fluorine or chlorine, and is substituted by one of the following radicals:

5-membered hetaryl, such as furyl, thienyl, pyrryl, pyrazolyl, imidazolyl, triazolyl, isoxazolyl, oxazolyl, isothiazolyl, thiazolyl or thiadiazolyl, which in turn may carry from one to four halogen atoms as stated above, preferably fluorine or chlorine, and/or one or two of the following radicals: $C_1$–$C_4$-alkyl, $C_1$–$C_4$-alkoxy, $C_1$–$C_4$-haloalkyl, $C_1$–$C_4$-haloalkoxy or $C_1$–$C_4$-alkylthio as stated specifically above;

$R^1$ is furthermore $C_2$–$C_6$-alkyl, in particular $C_2$–$C_4$-alkyl, which is substituted in the 2-position by $C_1$–$C_6$-alkoximino, for example methoximino, ethoximino or propoximino, $C_3$–$C_6$-alkenyloximino, such as 2-propenyloximino, 2-butenyloximino or 3-butenyloximino; $C_3$–$C_6$-haloalkenyloximino, such as 3,3-dichloro-2-propenyloximino or 2,3,3-trichloro-2-propenyloximino, or benzyloximino;

$R^1$ is furthermore $C_3$–$C_{12}$-cycloalkyl, in particular $C_3$–$C_7$-cycloalkyl, such as cyclopropyl, cyclobutyl, cyclopentyl, cyclohexyl or cycloheptyl, which may carry from one to five halogen atoms as stated above, in particular fluorine or chlorine, and/or one of the following radicals:

$C_1$–$C_4$-alkyl, $C_1$–$C_4$-alkoxy, $C_1$–$C_4$-alkylthio, cyano, $C_1$–$C_8$-alkylcarbonyl, $C_1$–$C_8$-alkoxycarbonyl, phenyl, phenoxy or phenylcarbonyl as stated specifically above, where the phenyl radicals in turn may be substituted, as stated, by halogen, in particular fluorine or chlorine, alkyl, haloalkyl, alkoxy, haloalkoxy and/or alkylthio;

$C_3$–$C_{12}$-cycloalkenyl, in particular $C_4$–$C_7$-cycloalkenyl, such as cyclobutenyl, cyclopentenyl, cyclohexenyl or cycloheptenyl, which can be substituted in the same way as the cycloalkyl group by halogen, alkyl, alkoxy, alkylthio, cyano, alkylcarbonyl, alkoxycarbonyl, phenyl, phenoxy or phenylcarbonyl;

$C_3$–$C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3 pentenyl, 2-methyl-3-pentenyl, 3-methyl-3 pentenyl, 4-methyl-3 pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl,1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, in particular 2-propenyl, 2-butenyl, 3-methyl-2-butenyl or 3-methyl-2-pentenyl;

$C_3$–$C_6$-alkynyl, such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, butynyl, 1,1-dimethyl-2-propynyl, 1-ethyl-2-propynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, preferably 2-propynyl, 2-butynyl, 1-methyl-2-propynyl or 1-methyl-2-butynyl, in particular 2-propynyl where these alkenyl and alkynyl groups may carry from one to five halogen atoms and/or one of the following radicals:

alkoxy, alkylthio, cyano, alkylcarbonyl, alkoxycarbonyl, phenyl, phenoxy or phenylcarbonyl as stated above;

$R^1$ is furthermore phenyl which is unsubstituted or mono-substituted to trisubstituted by $C_1$–$C_4$-alkyl or $C_1$–$C_4$-alkoxy, such as methyl, ethyl, propyl, butyl, methoxy, ethoxy, propoxy or butoxy, or phenyl substituted by from one to five halogen atoms, for example chlorine or fluorine;

$R^2$ one of the alkyl, haloalkyl, alkoxy, haloalkoxy or alkylthio groups or halogen atoms stated specifically for $R^1$, in particular chlorine, methyl, methoxy, ethoxy, difluoromethoxy or trifluoromethoxy;

X is nitrogen or $CR^6$, in which $R^6$ is hydrogen or, together with $R^3$, forms a 3-membered or 4-membered alkylene or alkenylene chain, in each of which a methylene group is replaced with oxygen, such as —$CH_2$—$CH_2$—O— —CH═CH—O—, —$CH_2$—$CH_2$—$CH_2$—O—, or —CH═CH—$CH_2$—O—, in particular hydrogen or —$CH_2$—$CH_2$—O—; this alkylene or alkenylene chain interrupted by oxygen may additionally contain one or more, for example one or two, substituents selected from the group consisting of $C_1$–$C_4$-alkyl, phenyl, $C_1$–$C_4$-alkoxy and $C_1$–$C_4$-alkoxycarbonyl, eg. methyl, methoxy, ethyl, ethoxy, methoxycarbonyl or ethoxycarbonyl;

$R^3$ is one of the $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio groups or halogen atoms stated for $R^1$, in particular chlorine, methyl, methoxy, ethoxy, difluoromethoxy or trifluoromethoxy, or is bonded to $R^6$ as stated above to form a 5-membered or 6-membered ring;

$R^4$ is $C_1$–$C_{10}$-alkyl as stated specifically for $R^1$, which may carry from one to five halogen atoms, such as fluorine, chlorine, bromine or iodine, in particular fluorine or chlorine and/or one of the following radicals: alkoxy, alkylthio, cyano, alkylcarbonyl, alkoxycarbonyl, phenyl, phenoxy or phenylcarbonyl as stated in general and in particular for $R^1$;

$C_1$–$C_{10}$-alkyl as stated above, which may carry from one to five halogen atoms as stated above, in particular fluorine or chlorine, and carries an unsubstituted or substituted 5-membered heteroaromatic structure as stated above for $R^1$;

$C_3$–$C_{12}$-cycloalkyl, in particular $C_3$–$C_7$-cycloalkyl, or $C_3$–$C_{12}$-cycloalkenyl, in particular $C_4$–$C_7$-cycloalkenyl, where a methylene group in the saturated or unsaturated ring may be replaced with an oxygen or sulfur atom, such as cyclopropyl, cyclobutyl, cyclopentyl, cyclohexyl, cycloheptyl, tetrahydrofuranyl, tetrahydrothienyl, tetrahydropyranyl or tetrahydrothiopyranyl; cyclpropenyl, cyclobutenyl, cyclopentenyl, cyclohexenyl, cycloheptenyl, dihydrofuranyl, dihydrothienyl, dihydropyranyl or dihydrothiopyranyl, where the cycloalkyl or cycloalkenyl radicals may be substituted by from one to five halogen atoms as stated above, in particular fluorine or chlorine, and/or one of the following radicals: $C_1$–$C_4$-alkyl, $C_1$–$C_4$-alkoxy, $C_1$–$C_4$-alkylthio, cyano, $C_1$–$C_8$-alkylcarbonyl, $C_1$–$C_8$-alkoxycarbonyl, phenyl, phenoxy or phenylcarbonyl as stated in general and in particular above;

$C_3$–$C_6$-alkenyl or $C_3$–$C_6$-alkynyl as stated for $R^1$, which may carry from one to five halogen atoms as stated above, in particular fluorine or chlorine, and/or one of the following radicals:

$C_1$–$C_4$-alkyl, $C_1$–$C_4$-alkoxy, $C_1$–$C_4$-alkylthio, cyano, $C_1$–$C_8$-alkylcarbonyl, $C_1$–$C_8$-alkoxycarbonyl, phenyl, phenoxy or phenylcarbonyl as stated in general and in particular above;

5-membered or 6-membered hetaryl, such as furyl, thienyl, pyrryl, pyrazolyl, imidazolyl, triazolyl, isoxazolyl, oxazolyl, isothiazolyl, thiazolyl or thiddiazolyl, pyridyl, pyrimidinyl, pyrazinyl, pyridazinyl or triazinyl, for example, 2-furanyl, 3-furanyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 3-pyrrolyl, 3-pyrazolyl, 4-pyrazolyl, 5-pyrazolyl, 2-pyridyl, 3-pyridyl, 4-pyridyl, oxa-2,4-diazolyl, oxa-3,4-diazolyl, thia-2,4-diazolyl, thia-3,4-diazolyl or triazolyl, where the heteroaromatic structures may carry from one to five halogen atoms as stated above, in particular fluorine or chlorine, and/or one of the following radicals: $C_1$–$C_4$-alkyl, $C_1$–$C_4$-alkoxy, $C_1$–$C_4$-alkylthio, cyano, $C_1$–$C_8$-alkylcarbonyl, $C_1$–$C_8$-alkoxycarbonyl, phenyl, phenoxy or phenylcarbonyl as stated in general and in particular above;

phenyl or naphthyl which may carry from one to five halogen atoms as stated above, in particular fluorine or chlorine, and/or one or two of the following radicals: $C_1$–$C_4$-alkyl, $C_1$–$C_4$-alkoxy, $C_1$–$C_4$-haloalkyl, $C_1$–$C_4$-haloalkoxy or $C_1$–$C_4$-alkylthio, as stated in general and in particular above;

or $R^4$ and $R^5$, together with the adjacent carbon atom, form a 3-membered to 6-membered ring which may contain a nitrogen or sulfur atom and is unsubstituted or, depending on the ring size, carries from one to three of the following radicals: $C_1$–$C_4$-alkyl, $C_1$–$C_4$-alkoxy, $C_1$–$C_4$-haloalkyl, $C_1$–$C_4$-haloalkoxy or $C_1$–$C_4$-alkylthio as stated in general and in particular above;

$R^5$ is $C_1$–$C_4$-alkyl, $C_1$–$C_4$-alkoxy, $C_1$–$C_4$-haloalkyl, $C_1$–$C_4$-haloalkoxy or $C_1$–$C_4$-alkylthio as stated in general and in particular above for $R^1$, or may furthermore be hydrogen, or $R^4$ together with $R^5$ forms the 3-membered to 6-membered ring as stated above, and Y and Z are each oxygen or sulfur.

Compounds of the formula I where $R^1$ is $C_1$–$C_4$-alkyl, eg. methyl or ethyl, $R^2$ is $C_1$–$C_4$-alkoxy, eg. methoxy, $R^5$ is hydrogen, Y is oxygen and X, Z, $R^3$ and $R^4$ have the abovementioned meanings are particularly preferred.

$R^3$ is particularly preferably $C_1$–$C_4$-alkoxy, eg. methoxy or ethoxy, halogen, eg. chlorine, or $C_1$–$C_4$-alkyl, eg. methyl or ethyl, or, where X is $CR^6$, together with $R^6$ forms an —$OCH_2CH_2$— chain.

X is preferably N, CH or $CR^6$, where $R^6$ is bonded to $R^3$, as stated for $R^3$.

Examples of particularly preferred compounds of the general formula I are summarized in Tables a and b below:

TABLE a

Thiocarboxylic acid derivatives of the formula I where Z is O

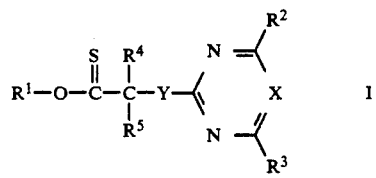

| $R^4$ | $R^5$ | $R^1$ | $R^2$ | $R^3$ | X | Y |
|---|---|---|---|---|---|---|
| Methyl | H | $CH_3$ | $OCH_3$ | $OCH_3$ | CH | O |
| Ethyl | H | $CH_3$ | $OCH_3$ | $OCH_3$ | CH | O |
| 1-Propyl | H | $CH_3$ | $OCH_3$ | $OCH_3$ | CH | O |
| 2-Propyl | H | $CH_3$ | $OCH_3$ | $OCH_3$ | CH | O |
| 1-Butyl | H | $CH_3$ | $OCH_3$ | $OCH_3$ | CH | O |
| 2-Butyl | H | $CH_3$ | $OCH_3$ | $OCH_3$ | CH | O |
| i-Butyl | H | $CH_3$ | $OCH_3$ | $OCH_3$ | CH | O |
| t-Butyl | H | $CH_3$ | $OCH_3$ | $OCH_3$ | CH | O |
| Cyclopropyl | H | $CH_3$ | $OCH_3$ | $OCH_3$ | CH | O |
| Cyclobutyl | H | $CH_3$ | $OCH_3$ | $OCH_3$ | CH | O |
| Cyclopentyl | H | $CH_3$ | $OCH_3$ | $OCH_3$ | CH | O |
| Cyclohexyl | H | $CH_3$ | $OCH_3$ | $OCH_3$ | CH | O |
| 1-Methylcyclopropyl | H | $CH_3$ | $OCH_3$ | $OCH_3$ | CH | O |
| 1-Phenyl-1-ethyl | H | $CH_3$ | $OCH_3$ | $OCH_3$ | CH | O |
| 2-Phenyl-2-propyl | H | $CH_3$ | $OCH_3$ | $OCH_3$ | CH | O |
| 2-Fluor-2-propyl | H | $CH_3$ | $OCH_3$ | $OCH_3$ | CH | O |
| Phenyl | H | $CH_3$ | $OCH_3$ | $OCH_3$ | CH | O |
| 2-Fluorophenyl | H | $CH_3$ | $OCH_3$ | $OCH_3$ | CH | O |
| 3-Chlorphenyl | H | $CH_3$ | $OCH_3$ | $OCH_3$ | CH | O |
| 4-Bromophenyl | H | $CH_3$ | $OCH_3$ | $OCH_3$ | CH | O |
| 2-Methoxyphenyl | H | $CH_3$ | $OCH_3$ | $OCH_3$ | CH | O |
| 4-Methoxyphenyl | H | $CH_3$ | $OCH_3$ | $OCH_3$ | CH | O |
| 1-Naphthyl | H | $CH_3$ | $OCH_3$ | $OCH_3$ | CH | O |
| 2-Naphthyl | H | $CH_3$ | $OCH_3$ | $OCH_3$ | CH | O |
| 2-Pyridyl | H | $CH_3$ | $OCH_3$ | $OCH_3$ | CH | O |
| 3-Pyridyl | H | $CH_3$ | $OCH_3$ | $OCH_3$ | CH | O |
| 2-Thienyl | H | $CH_3$ | $OCH_3$ | $OCH_3$ | CH | O |
| 3-Isooxazolyl | H | $CH_3$ | $OCH_3$ | $OCH_3$ | CH | O |
| 2-Thiazolyl | H | $CH_3$ | $OCH_3$ | $OCH_3$ | CH | O |
| Methyl | $CH_3$ | $CH_3$ | $OCH_3$ | $OCH_3$ | CH | O |

TABLE a-continued

Thiocarboxylic acid derivatives of the formula I where Z is O

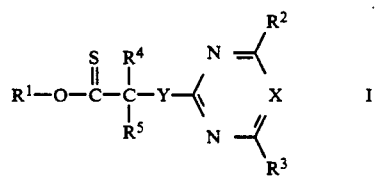

| R⁴ | R⁵ | R¹ | R² | R³ | X | Y |
|---|---|---|---|---|---|---|
| Ethyl | CH₃ | CH₃ | OCH₃ | OCH₃ | CH | O |
| 1-Propyl | CH₃ | CH₃ | OCH₃ | OCH₃ | CH | O |
| 2-Propyl | CH₃ | CH₃ | OCH₃ | OCH₃ | CH | O |
| 1-Butyl | CH₃ | CH₃ | OCH₃ | OCH₃ | CH | O |
| 2-Butyl | CH₃ | CH₃ | OCH₃ | OCH₃ | CH | O |
| i-Butyl | CH₃ | CH₃ | OCH₃ | OCH₃ | CH | O |
| t-Butyl | CH₃ | CH₃ | OCH₃ | OCH₃ | CH | O |
| Cyclopropyl | CH₃ | CH₃ | OCH₃ | OCH₃ | CH | O |
| Methyl | H | CH₂CH₃ | OCH₃ | OCH₃ | CH | O |
| Ethyl | H | CH₂CH₃ | OCH₃ | OCH₃ | CH | O |
| 1-Propyl | H | CH₂CH₃ | OCH₃ | OCH₃ | CH | O |
| 2-Propyl | H | CH₂CH₃ | OCH₃ | OCH₃ | CH | O |
| 1-Butyl | H | CH₂CH₃ | OCH₃ | OCH₃ | CH | O |
| 2-Butyl | H | CH₂CH₃ | OCH₃ | OCH₃ | CH | O |
| i-Butyl | H | CH₂CH₃ | OCH₃ | OCH₃ | CH | O |
| t-Butyl | H | CH₂CH₃ | OCH₃ | OCH₃ | CH | O |
| Cyclopropyl | H | CH₂CH₃ | OCH₃ | OCH₃ | CH | O |
| Methyl | H | CH₃ | OCH₃ | OCH₃ | CH | S |
| Ethyl | H | CH₃ | OCH₃ | OCH₃ | CH | S |
| 1-Propyl | H | CH₃ | OCH₃ | OCH₃ | CH | S |
| 2-Propyl | H | CH₃ | OCH₃ | OCH₃ | CH | S |
| 1-Butyl | H | CH₃ | OCH₃ | OCH₃ | CH | S |
| 2-Butyl | H | CH₃ | OCH₃ | OCH₃ | CH | S |
| i-Butyl | H | CH₃ | OCH₃ | OCH₃ | CH | S |
| t-Butyl | H | CH₃ | OCH₃ | OCH₃ | CH | S |
| Cyclopropyl | H | CH₃ | OCH₃ | OCH₃ | CH | S |
| Methyl | H | CH₃ | OCH₃ | OCH₃ | N | O |
| Ethyl | H | CH₃ | OCH₃ | OCH₃ | N | O |
| 1-Propyl | H | CH₃ | OCH₃ | OCH₃ | N | O |
| 2-Propyl | H | CH₃ | OCH₃ | OCH₃ | N | O |
| 1-Butyl | H | CH₃ | OCH₃ | OCH₃ | N | O |
| 2-Butyl | H | CH₃ | OCH₃ | OCH₃ | N | O |
| i-Butyl | H | CH₃ | OCH₃ | OCH₃ | N | O |
| t-Butyl | H | CH₃ | OCH₃ | OCH₃ | N | O |
| Cyclopropyl | H | CH₃ | OCH₃ | OCH₃ | N | O |
| Methyl | H | CH₃ | OCH₃ | OCH₂CH₂ | | O |
| Ethyl | H | CH₃ | OCH₃ | OCH₂CH₂ | | O |
| 1-Propyl | H | CH₃ | OCH₃ | OCH₂CH₂ | | O |
| 2-Propyl | H | CH₃ | OCH₃ | OCH₂CH₂ | | O |
| 1-Butyl | H | CH₃ | OCH₃ | OCH₂CH₂ | | O |
| 2-Butyl | H | CH₃ | OCH₃ | OCH₂CH₂ | | O |
| i-Butyl | H | CH₃ | OCH₃ | OCH₂CH₂ | | O |
| t-Butyl | H | CH₃ | OCH₃ | OCH₂CH₂ | | O |
| Cyclopropyl | H | CH₃ | OCH₃ | OCH₂CH₂ | | O |
| 2-Propyl | H | 1-Propyl | OCH₃ | OCH₃ | CH | O |
| 2-Propyl | H | 2-Propyl | OCH₃ | OCH₃ | CH | O |
| 2-Propyl | H | 1-Butyl | OCH₃ | OCH₃ | CH | O |
| 2-Propyl | H | 2-Butyl | OCH₃ | OCH₃ | CH | O |
| 2-Propyl | H | i-Butyl | OCH₃ | OCH₃ | CH | O |
| 2-Propyl | H | Cyclopropyl | OCH₃ | OCH₃ | CH | O |
| 2-Propyl | H | Cyclobutyl | OCH₃ | OCH₃ | CH | O |
| 2-Propyl | H | Cyclopentyl | OCH₃ | OCH₃ | CH | O |
| 2-Propyl | H | Cyclohexyl | OCH₃ | OCH₃ | CH | O |
| 2-Propyl | H | Benzyl | OCH₃ | OCH₃ | CH | O |
| 2-Propyl | H | Allyl | OCH₃ | OCH₃ | CH | O |
| 2-Propyl | H | Propargyl | OCH₃ | OCH₃ | CH | O |
| —CH₂—CH₂—O—CH₃ | H | CH₃ | OCH₃ | OCH₃ | CH | O |
| —CH₂—S—CH₃ | CH₃ | CH₃ | OCH₃ | OCH₃ | CH | O |
| 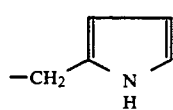 | H | C₂H₅ | OCH₃ | OCH₃ | CH | O |
| 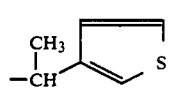 | H | CH₃ | OC₂H₅ | OCH₃ | CH | O |

TABLE a-continued
Thiocarboxylic acid derivatives of the formula I where Z is O

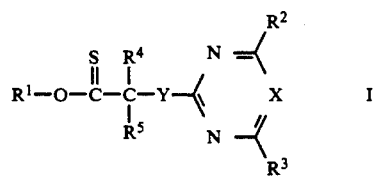

| R⁴ | R⁵ | R¹ | R² | R³ | X | Y |
|---|---|---|---|---|---|---|
| ![pyrazole-dimethyl] (CH₃)₂C- attached to pyrazole NH | H | CH₃ | OCH₃ | Cl | CH | O |
| -CH₂- thiazole | H | CH₃ | OCH₃ | OCH₃ | N | O |
| -CH₂- isoxazole with isopropyl | H | CH₃ | OCH₃ | OCH₃ | N | S |
| tetrahydrothiopyran-yl | H | CH₃ | OCH₃ | OCH₂CH₂ | | O |
| tetrahydropyran-yl | H | CH₃ | OCF₃ | OCH₃ | CH | O |
| dihydrothiophene-yl | H | 2-Propyl | OCH₃ | OCH₃ | CH | O |
| cyclohexenyl | CH₂CH₃ | CH₃ | OCH₃ | OCH₃ | CH | O |
| -CH=CH-CH₃ | H | CH₃ | OCH₃ | CH₃ | CH | O |
| -C≡CH | H | CH₃ | SCH₃ | OCH₃ | CH | O |

TABLE b
Thiocarboxylic acid derivatives of the formula I where Z is S

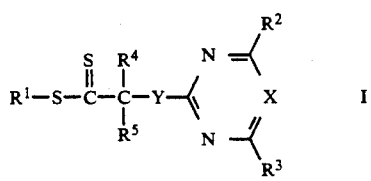

| R⁴ | R⁵ | R¹ | R² | R³ | X | Y |
|---|---|---|---|---|---|---|
| Methyl | H | CH₃ | OCH₃ | OCH₃ | CH | O |
| Ethyl | H | CH₃ | OCH₃ | OCH₃ | CH | O |
| 1-Propyl | H | CH₃ | OCH₃ | OCH₃ | CH | O |
| 2-Propyl | H | CH₃ | OCH₃ | OCH₃ | CH | O |
| 1-Butyl | H | CH₃ | OCH₃ | OCH₃ | CH | O |
| 2-Butyl | H | CH₃ | OCH₃ | OCH₃ | CH | O |
| i-Butyl | H | CH₃ | OCH₃ | OCH₃ | CH | O |
| t-Butyl | H | CH₃ | OCH₃ | OCH₃ | CH | O |

TABLE b-continued

Thiocarboxylic acid derivatives of the formula I where Z is S

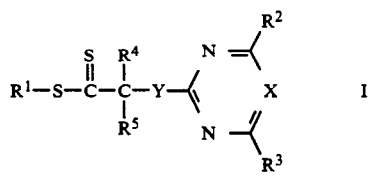

| R⁴ | R⁵ | R¹ | R² | R³ | X | Y |
|---|---|---|---|---|---|---|
| Cyclopropyl | H | CH₃ | OCH₃ | OCH₃ | CH | O |
| Cyclobutyl | H | CH₃ | OCH₃ | OCH₃ | CH | O |
| Cyclopentyl | H | CH₃ | OCH₃ | OCH₃ | CH | O |
| Cyclohexyl | H | CH₃ | OCH₃ | OCH₃ | CH | O |
| 1-Methylcyclopropyl | H | CH₃ | OCH₃ | OCH₃ | CH | O |
| 1-Phenyl-1-ethyl | H | CH₃ | OCH₃ | OCH₃ | CH | O |
| 2-Phenyl-2-propyl | H | CH₃ | OCH₃ | OCH₃ | CH | O |
| 2-Fluor-2-propyl | H | CH₃ | OCH₃ | OCH₃ | CH | O |
| Phenyl | H | CH₃ | OCH₃ | OCH₃ | CH | O |
| 2-Fluorophenyl | H | CH₃ | OCH₃ | OCH₃ | CH | O |
| 3-Chlorphenyl | H | CH₃ | OCH₃ | OCH₃ | CH | O |
| 4-Bromphenyl | H | CH₃ | OCH₃ | OCH₃ | CH | O |
| 2-Methoxyphenyl | H | CH₃ | OCH₃ | OCH₃ | CH | O |
| 4-Methoxyphenyl | H | CH₃ | OCH₃ | OCH₃ | CH | O |
| 1-Naphthyl | H | CH₃ | OCH₃ | OCH₃ | CH | O |
| 2-Naphthyl | H | CH₃ | OCH₃ | OCH₃ | CH | O |
| 2-Pyridyl | H | CH₃ | OCH₃ | OCH₃ | CH | O |
| 3-Pyridyl | H | CH₃ | OCH₃ | OCH₃ | CH | O |
| 2-Thienyl | H | CH₃ | OCH₃ | OCH₃ | CH | O |
| 3-Isooxazolyl | H | CH₃ | OCH₃ | OCH₃ | CH | O |
| 2-Thiazolyl | H | CH₃ | OCH₃ | OCH₃ | CH | O |
| Methyl | CH₃ | CH₃ | OCH₃ | OCH₃ | CH | O |
| Ethyl | CH₃ | CH₃ | OCH₃ | OCH₃ | CH | O |
| 1-Propyl | CH₃ | CH₃ | OCH₃ | OCH₃ | CH | O |
| 2-Propyl | CH₃ | CH₃ | OCH₃ | OCH₃ | CH | O |
| 1-Butyl | CH₃ | CH₃ | OCH₃ | OCH₃ | CH | O |
| 2-Butyl | CH₃ | CH₃ | OCH₃ | OCH₃ | CH | O |
| i-Butyl | CH₃ | CH₃ | OCH₃ | OCH₃ | CH | O |
| t-Butyl | CH₃ | CH₃ | OCH₃ | OCH₃ | CH | O |
| Cyclopropyl | CH₃ | CH₃ | OCH₃ | OCH₃ | CH | O |
| Methyl | H | CH₂CH₃ | OCH₃ | OCH₃ | CH | O |
| Ethyl | H | CH₂CH₃ | OCH₃ | OCH₃ | CH | O |
| 1-Propyl | H | CH₂CH₃ | OCH₃ | OCH₃ | CH | O |
| 2-Propyl | H | CH₂CH₃ | OCH₃ | OCH₃ | CH | O |
| 1-Butyl | H | CH₂CH₃ | OCH₃ | OCH₃ | CH | O |
| 2-Butyl | H | CH₂CH₃ | OCH₃ | OCH₃ | CH | O |
| i-Butyl | H | CH₂CH₃ | OCH₃ | OCH₃ | CH | O |
| t-Butyl | H | CH₂CH₃ | OCH₃ | OCH₃ | CH | O |
| Cyclopropyl | H | CH₂CH₃ | OCH₃ | OCH₃ | CH | O |
| Methyl | H | CH₃ | OCH₃ | OCH₃ | CH | S |
| Ethyl | H | CH₃ | OCH₃ | OCH₃ | CH | S |
| 1-Propyl | H | CH₃ | OCH₃ | OCH₃ | CH | S |
| 2-Propyl | H | CH₃ | OCH₃ | OCH₃ | CH | S |
| 1-Butyl | H | CH₃ | OCH₃ | OCH₃ | CH | S |
| 2-Butyl | H | CH₃ | OCH₃ | OCH₃ | CH | S |
| i-Butyl | H | CH₃ | OCH₃ | OCH₃ | CH | S |
| t-Butyl | H | CH₃ | OCH₃ | OCH₃ | CH | S |
| Cyclopropyl | H | CH₃ | OCH₃ | OCH₃ | CH | S |
| Methyl | H | CH₃ | OCH₃ | OCH₃ | N | O |
| Ethyl | H | CH₃ | OCH₃ | OCH₃ | N | O |
| 1-Propyl | H | CH₃ | OCH₃ | OCH₃ | N | O |
| 2-Propyl | H | CH₃ | OCH₃ | OCH₃ | N | O |
| 1-Butyl | H | CH₃ | OCH₃ | OCH₃ | N | O |
| 2-Butyl | H | CH₃ | OCH₃ | OCH₃ | N | O |
| i-Butyl | H | CH₃ | OCH₃ | OCH₃ | N | O |
| t-Butyl | H | CH₃ | OCH₃ | OCH₃ | N | O |
| Cyclopropyl | H | CH₃ | OCH₃ | OCH₃ | N | O |
| Methyl | H | CH₃ | OCH₃ | OCH₂CH₂ | | O |
| Ethyl | H | CH₃ | OCH₃ | OCH₂CH₂ | | O |
| 1-Propyl | H | CH₃ | OCH₃ | OCH₂CH₂ | | O |
| 2-Propyl | H | CH₃ | OCH₃ | OCH₂CH₂ | | O |
| 1-Butyl | H | CH₃ | OCH₃ | OCH₂CH₂ | | O |
| 2-Butyl | H | CH₃ | OCH₃ | OCH₂CH₂ | | O |
| i-Butyl | H | CH₃ | OCH₃ | OCH₂CH₂ | | O |
| t-Butyl | H | CH₃ | OCH₃ | OCH₂CH₂ | | O |
| Cyclopropyl | H | CH₃ | OCH₃ | OCH₂CH₂ | | O |
| 2-Propyl | H | 1-Propyl | OCH₃ | OCH₃ | CH | O |
| 2-Propyl | H | 2-Propyl | OCH₃ | OCH₃ | CH | O |
| 2-Propyl | H | 1-Butyl | OCH₃ | OCH₃ | CH | O |

TABLE b-continued

Thiocarboxylic acid derivatives of the formula I where Z is S

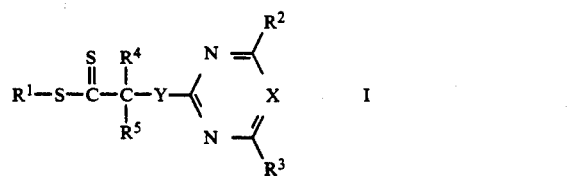

| R⁴ | R⁵ | R¹ | R² | R³ | X | Y |
|---|---|---|---|---|---|---|
| 2-Propyl | H | 2-Butyl | OCH₃ | OCH₃ | CH | O |
| 2-Propyl | H | i-Butyl | OCH₃ | OCH₃ | CH | O |
| 2-Propyl | H | Cyclopropyl | OCH₃ | OCH₃ | CH | O |
| 2-Propyl | H | Cyclobutyl | OCH₃ | OCH₃ | CH | O |
| 2-Propyl | H | Cyclopentyl | OCH₃ | OCH₃ | CH | O |
| 2-Propyl | H | Cyclohexyl | OCH₃ | OCH₃ | CH | O |
| 2-Propyl | H | Benzyl | OCH₃ | OCH₃ | CH | O |
| 2-Propyl | H | Allyl | OCH₃ | OCH₃ | CH | O |
| 2-Propyl | H | Propargyl | OCH₃ | OCH₃ | CH | O |
| —CH₂—CH₂—O—CH₃ | H | CH₃ | OCH₃ | OCH₃ | CH | O |
| —CH₂—S—CH₃ | CH₃ | CH₃ | OCH₃ | OCH₃ | CH | O |
| —CH₂-(pyrrole) | H | CH₂CH₃ | OCH₃ | OCH₃ | CH | O |
| —CH(CH₃)-(thiophene) | H | CH₃ | OC₂H₅ | OCH₃ | CH | O |
| —C(CH₃)=CH—NH—N=(imidazole) | H | CH₃ | OCH₃ | Cl | CH | O |
| —CH₂-(thiazole) | H | CH₃ | OCH₃ | OCH₃ | N | O |
| —CH₂-(isoxazole with i-Pr) | H | CH₃ | OCH₃ | OCH₃ | N | S |
| -(tetrahydrothiopyran) | H | CH₃ | OCH₃ | OCH₂CH₂ | | O |
| -(tetrahydropyran) | H | CH₃ | OCF₃ | OCH₃ | CH | O |
| -(dihydrothiopyran) | H | 2-Propyl | OCH₃ | OCH₃ | CH | O |
| -(cyclohexyl) | CH₂CH₃ | CH₃ | OCH₃ | OCH₃ | CH | O |
| —CH=CH—CH₃ | H | CH₃ | OCH₃ | CH₃ | CH | O |
| —C≡CH | H | CH₃ | SCH₃ | OCH₃ | CH | O |

The compounds of the general formula I or the herbicides or growth regulators containing them can be used, for example, in the form of directly sprayable solutions, powders, suspensions, including concentrated aqueous, oily or other suspensions or dispersions, emulsions, oil dispersions, pastes, dusting agents, broadcasting agents or granules, by spraying, nebulizing, dusting, broadcasting or pouring. The application forms depend on the intended uses; they should in any case ensure a very fine distribution of the novel active ingredients.

The compounds I are suitable in general for the preparation of directly sprayable solutions, emulsions, pastes or oil dispersions. Suitable inert additives are mineral oil fractions having a medium to high boiling point, such as kerosene or diesel oil, as well as coal tar oils and oils of vegetable or animal origin, aliphatic, cyclic and aromatic hydrocarbons, for example toluene, xylene, paraffin, tetrahydronaphthalene, alkylated naphthalenes or derivatives thereof, methanol, ethanol, propanol, butanol, cyclohexanol, cyclohexanone, chlorobenzene, isophorone or strongly polar solvents, such as N,N-dimethylformamide, dimethyl sulfoxide, N-methylpyrrolidone or water.

Aqueous application forms can be prepared from emulsion concentrates, dispersions, pastes, wettable powders or water-dispersible granules by adding water. For the preparation of emulsions, pastes or oil dispersions, the substrates, as such or dissolved in an oil or solvent, can be homogenized in water by means of wetting agents, adherents, dispersants or emulsifiers. However, it is also possible to prepare concentrates which consist of active ingredient, wetting agents, adherents, dispersants or emulsifiers and possibly solvents or oil and which are suitable for dilution with water.

Suitable surfactants are alkali metal, alkaline earth metal and ammonium salts of aromatic sulfonic acids, for example lignin-, phenol-, naphthalene- and dibutylnaphthalenesullonic acid, and of fatty acids, alkylsulfonates, alkylarylsulfonates, alkylsulfates, lauryl ether sulfates and fatty alcohol sulfates, and salts of sulfated hexa-, hepta- and octadecanols, and of fatty alcohol glycol ethers, condensates of sulfonated naphthalene and its derivatives with formaldehyde, condensates of naphthalene or of naphthalenesulfonic acids with phenol and formaldehyde, polyoxyethylene octylphenol ethers, ethoxylated isooctyl-, octyl- or nonylphenol, alkylphenol polyglycol ethers, tributylphenol polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetals, sorbitol esters, ligninsulfite waste liquors or methylcellulose.

Powders, broadcasting agents and dusting agents can be prepared by mixing or milling the active ingredients together with a solid carrier.

Granules, for example, coated, impregnated and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate and ureas, and vegetable products, such as grain flours, bark meal, wood meal and nutshell meal, cellulosic powders or other solid carriers.

The formulations contain from 0.01 to 95, preferably from 0.5 to 90, % by weight of active ingredient. The active ingredients are used in a purity of from 90 to 100%, preferably from 95 to 100% (according to the NMR spectrum).

The novel compounds I may be formulated, for example, as follows:

I. 90 parts by weight of compound No. 1.001 are mixed with 10 parts by weight of N-methyl-α-pyrrolidone, and a solution which is suitable for use in the form of very small drops is obtained.

II. 20 parts by weight of compound No. 1.002 are dissolved in a mixture which consists of 80 parts by weight of xylene, 10 parts by weight of the adduct of from 8 to 10 mol of ethylene oxide with 1 mol of N-monoethanololeamide, 5 parts by weight of calcium salt of dodecylbenzenesulfonic acid and 5 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

III. 20 parts by weight of compound No. 1.007 are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

IV. 20 parts by weight of active ingredient No. 1.008 are dissolved in a mixture which consists of 25 parts by weight of cyclohexanone, 65 parts by weight of a mineral oil fraction boiling within a range from 210° to 280° C. and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

V. 20 parts by weight of active ingredient No. 1.009 are thoroughly mixed with 3 parts by weight of the sodium salt of diisobutylnaphthalene-α-sulfonic acid, 1 part by weight of the sodium salt of a ligninsulfonic acid obtained from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

VI. 3 parts by weight of active ingredient No. 1.004 are mixed with 97 parts by weight of finely divided kaolin. A dusting agent which contains 3% by weight of the active ingredient is obtained in this manner.

VII. 30 parts by weight of active ingredient No. 1.003 are thoroughly mixed with a mixture of 92 parts by weight of silica gel powder and 8 parts by weight of liquid paraffin which was sprayed onto the surface of the silica gel. A formulation of the active ingredient having good adhesion is obtained in this manner.

VIII. 20 parts by weight of active ingredient No. 1.001 are thoroughly mixed with 2 parts by weight of the calcium salt of dodecylbenzenesulfonic acid, 8 parts by weight of the fatty alcohol polyglycol ether, 2 parts by weight of the sodium salt of a phenol sulfonic acid/urea/formaldehyde condensate and 68 parts by weight of a paraffinic mineral oil. A stable oily dispersion is obtained.

The herbicides and growth regulators or the active ingredients can be applied by the preemergence or postemergence method. If the active ingredients are less well tolerated by certain crops, or if it is intended that these plants should continue to grow as far as possible unaffected, it is possible to use application methods in which the agents are sprayed with the aid of the sprayers so that the leaves of the sensitive crops are as far as possible not affected while the active ingredients reach the leaves of undesirable plants growing underneath or the uncovered soil surface (post-directed, lay-by).

The application rates of active ingredient are from 0.001 to 3, preferably from 0.01 to 2, kg/ha of active ingredient (a.i.), depending on the aim of control, the season, the target plants and the state of growth.

The compounds of the formula I can influence virtually all stages of development of a plant in different ways and are therefore also used as growth regulators. However, the wide range of action of the plant growth regulators depends in particular a) on the plant species and variety,
b) on the time of application, based on the stage of development of the plant, and on the season,
c) on the application site and method (for example seed dressing, soil treatment, foliage application or trunk injection in the case of trees),
d) on climatic factors, for example temperature and amount of precipitation, as well as length of day and light intensity,
e) on the soil characteristics (including fertilizer application),
f) on the formulation or application form of the active ingredient and finally
g) on the concentrations of active ingredient used.

From the number of different potential applications of the novel plant growth regulators of the formula I in plant cultivation, in agriculture and in horticulture, a few are mentioned below.

A. The vegetative growth of the plants can be greatly inhibited with the compounds which can be used according to the invention, this being evident in particular in a reduction in the growth in length. The treated plants accordingly have stunted growth; in addition, a darker leaf coloration is observed.

A reduced intensity of growth of grasses along road edges, hedges and canal banks and on lawn areas, such as parks, sports grounds and orchards, ornamental lawns and airfields, proves to be advantageous in practice, so that labor-intensive and expensive cutting of grass can be reduced.

The increase in the stability of crops susceptible to lodging, such as cereals, rice, corn, sunflowers and soybean, is also of economic interest. The resulting shortening of the stem reduces or eliminates the danger of lodging (bending) of plants under unfavorable weather conditions prior to harvesting.

The use of growth regulators for inhibiting the growth in length and for changing the time of ripening in the case of cotton is also important. This permits completely mechanized harvesting of this important crop.

In the case of fruit trees and other trees, the growth regulators permit a saving of pruning costs. In addition, the alternation of fruit trees can be broken by growth regulators.

By using growth regulators, it is also possible to increase or inhibit the lateral branching of plants. This is of interest if it is intended to inhibit the formation of side shoots in favor of leaf growth, for example in tobacco plants.

Furthermore, the frost resistance can be considerably increased by growth regulators, for example in winter rape. On the one hand, the growth in length and the development of a leaf or plant mass which is too luxurious (and hence particularly susceptible to frost) are inhibited. On the other hand, the young rape plants are held back in the vegetative stage of development after sowing and before the onset of the winter frosts, in spite of favorable growth conditions. This also eliminates the danger of frost for plants which tend to exhibit premature termination of the inhibition of blooming and to go over into the generative phase. In other crops too, for example winter cereals, it is advantageous if the stocks are well tillered by treatment with novel compounds in the f all but do not start the winter with too luxurious a growth. The high sensitivity to frost and, owing to the relatively small leaf or plant mass, attack by various diseases (for example fungal disease) can thus be prevented. In many crops, the inhibition of vegetative growth also permits denser planting of the soil so that a higher yield can be achieved, based on the soil area.

B. Higher yields of both plant parts and plant ingredients can be obtained with growth regulators. For example, it is possible to induce the growth of larger amounts of buds, blooms, leaves, fruits, seeds, roots and tubers, to increase the content of sugar in sugar beet, sugar cane and citrus fruits, to increase the protein content in cereals or soybean or to stimulate rubber trees to produce a greater flow of latex.

The compounds of the formula I can increase yields by intervening in the plant metabolism or by promoting or inhibiting the vegetative and/or generative growth.

C. Finally, with plant growth regulators, it is possible both to shorten or lengthen the stages of development and to accelerate or retard the ripening of the harvested plant parts before or after harvesting.

For example, it is of economic interest to facilitate harvesting, which is permitted by concentrated dropping or a reduction in the adhesion to the tree in the case of citrus fruits, olives or other species and varieties of pomes, drupes and hardshelled fruit. The same mechanism, ie. promotion of the formation of abscission tissue between the fruit or leaf part and the shoot part of the plant is also important for readily controllable defoliation of crops, for example cotton.

D. Furthermore, the water consumption of plants can be reduced with growth regulators. This is important in particular for agricultural areas which have to be artificially irrigated at high cost, for example in arid or semiarid regions. By using the novel substances, it is possible to reduce the intensity of irrigation and hence to carry out more economical farming. Better utilization of the existing water is achieved under the influence of growth regulators because, inter alia, the opening of the stomata is changed, a thicker epidermis and cuticula are formed, root penetration of the soil is improved and the microclimate in the plant stock is advantageously affected by more compact growth.

E. Furthermore, the growth of undesirable plants can be restricted with the growth regulators of the formula I. In field crops, the competitiveness of weeds and gramineous weeds with respect to the crops can thus be reduced without there being a direct herbicidal action. It is also possible, for example in orchards or vineyards, greatly to reduce the competitive power of the undergrowth in favor of the crops without killing the corresponding grasses and herbaceous plants. Cohesive ground cover and hence, for example, better soil vitality and protection from erosion are achieved in this manner.

The growth regulators of the formula I which are to be used according to the invention can be supplied to the crops both through the seed (as the seed dressing) and via the soil, ie. through the roots and, particularly preferably, by spraying via the foliage.

Owing to the good toleration by plants, the application rate can be greatly varied.

In view of the wide range of application methods, the novel compounds or agents containing them can also be used in a number of crops for eliminating undesirable plants. For example, the following crops are suitable:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Brassica napus var. napus | rapeseed |
| Brassica napus var. napobrassica | swedes |
| Camellia sinensis | tea plants |
| Carthamus tinctorius | safflower |
| Carya illinoinensis | pecan trees |
| Citrus limon | lemons |
| Citrus sinensis | orange trees |
| Coffea arabica (Coffea canephora, Coffea liberica) | coffee plants |
| Cucumis sativus | cucumbers |
| Cynodon dactylon | Bermuda grass in turf and lawns |
| Daucus carota | carrots |
| Elaeis guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Hevea brasiliensis | rubber plants |
| Hordeum vulgare | barley |
| Humulus lupulus | hops |
| Ipomoea batatas | sweet potatoes |
| Juglans regia | walnut trees |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Musa spp. | banana plants |
| Nicotiana tabacum (N. rustica) | tobacco |
| Olea europaea | olive trees |
| Oryza sativa | rice |
| Phaseolus lunatus | limabeans |
| Phaseolus vulgaris | snapbeans, green beans, dry beans |
| Picea abies | Norway spruce |
| Pinus spp. | pine trees |
| Pisum sativum | English peas |
| Prunus avium | cherry trees |
| Prunus persica | peach trees |
| Pyrus communis | pear trees |
| Ribes sylvestre | redcurrants |
| Ricinus communis | castor-oil plants |
| Saccharum officinarum | sugar cane |
| Secale cereale | rye |
| Solanum tuberosum | Irish potatoes |
| Sorghum bicolor (s. vulgare) | sorghum |
| Theobroma cacao | cacao plants |
| Trifolium pratense | red clover |
| Triticum aestivum | wheat |
| Triticum durum | durum wheat |
| Vicia faba | tick beans |
| Vitis vinifera | grapes |
| Zea mays | Indian corn, sweet corn, maize |

To extend the action spectrum and to achieve synergistic effects, the thiocarboxylic acid derivatives I can be mixed, and applied together with, a larger number of other groups of herbicidal or growth-regulating active ingredients. For example, diazines, 4H-3,1-benzoxazine derivatives, benzothiadiazinone, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives, quinolinecarboxylic acid derivatives, sulfonylureas, aryloxy- and hetaryloxyphenoxypropionic acids and their salts, esters and amides and others are suitable components for the mixture.

Further suitable growth regulators include quaternary ammonium compounds, triazoles, cyclohexanetriones, imidazoles, norbornanodiazetenes, 4-pyridines, ethephone, abscissic acid and structures derived therefrom.

It may also be useful to apply the novel compounds I, alone or in combination with other herbicides, also as a mixture together with further crop protection agents, for example with pesticides or agents for controlling phytopathogenic fungi or bacteria. The miscibility with mineral salt solutions which are used for eliminating nutrient and trace element deficiencies is also of interest. Nonphytotoxic oils and oil concentrates may also be added. Synthesis Examples:

EXAMPLE 1

Preparation of nitriles of the formula IV 2-(4,6-Dimethoxypyrimidin-2-yl)-oxy-3,3-dimethylbutyronitrile 29.5 g (0.14 mol) of 2-methylsulfonyl-4,6-dimethoxypyrimidine were suspended in 180 ml of absolute dimethylformamide, and 20 g (0.18 mol) of 3,3-dimethyl-2-hydroxybutyronitrile were added. 5.2 g of 80% strength sodium hydride were then added a little at a time at 0° C., and the mixture was stirred for 3 hours at 60° C. After cooling, 10 g of acetic acid and 20 ml of water were added and the reaction mixture was poured onto 500 ml of water. The resulting precipitate was filtered off under suction and dried. 32.4 g of a white powder having a melting point of 88°-89° C. were obtained (yield: 92% of theory).

All compounds of the formula IV in which Y is oxygen can be prepared in a similar manner from cyanohydrins of the formula II and compounds of the formula III.

EXAMPLE 2

Preparation of thioamides V 2-(4,6-Dimethoxypyrimidin-2-yl)-oxy-3,3-dimethylthiobutyramide 16.5 g (0.066 mol) of 2-(4,6-dimethoxypyrimidin-2-yl)-oxy-3,3-dimethylbutyronitrile were dissolved in 150 ml of absolute dimethylformamide, and 2.5 g (0.033 mol) of diethylamine were added. Thereafter, hydrogen sulfide was passed through the solution at 55° C. for about 3 hours and stirring was carried out for 1 hour at this temperature. The reaction mixture was poured onto 1.2 l of ice water and the resulting precipitate was filtered off under suction and dried. 18 g of a white powder having a melting point of 187°–189° C. were obtained (yield: 96% of theory).

All nitriles of the general formula IV can be converted into the thioamides V in a similar manner.

EXAMPLE 3

Conversion of the thioamides into thiocarboxylic acid derivatives I

Thiomethyl 2-(4,6-dimethoxypyrimidin-2-yl)-oxy-3,3-dimethylthiobutyrate 18 g (0.063 mol) of 2-(4,6-dimethoxypyrimidin-2-yl)-oxy-3,3-dimethylthiobutyramide were dissolved in 200 ml of absolute dichloromethane under argon, and 10 g (0.070 mol) of trimethyloxonium tetrafluoborate were added a little at a time at 0° C. After the mixture had been stirred overnight at room temperature, the solvent was distilled off, the residue was suspended in 250 ml of absolute methyl tetrabutyl ether and hydrogen sulfide was passed through the solution for about 5 hours after the addition of 70 ml of absolute pyridine at 0° C. After the mixture had been stirred overnight at room temperature, 100 ml of water were added and the mixture was extracted twice with ethyl acetate. The organic phase was dried over magnesium sulfate and the solvent was then removed under reduced pressure. Recrystallization from ethanol gave 6 g of yellow crystals having a melting point of 91°–93° C. (yield: 30% of theory).

All compounds of the general formula I in which Y is oxygen can be prepared in a similar manner.

EXAMPLE 4

General method for reacting carboxylic acid derivatives of the formula VII with Lawesson's reagent 0.01 mol of a carboxylic acid derivative VII and 0.012 mol of Lawesson's reagent in 10 ml of xylene are heated at 140° C. for about 8 hours. After cooling, the mixture is purified directly by column chromatography.

The thiocarboxylic acid derivatives shown in

TABLE 1

Thiocarboxylic acid derivatives of the formula I where Y is O and Z is S

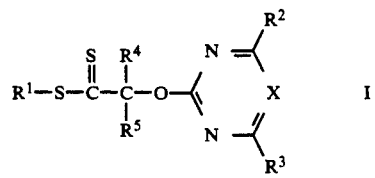

| Nr. | $R^4$ | $R^5$ | $R^1$ | $R^2$ | $R^3$ | X | Phys. Daten Fp [°C.] |
|---|---|---|---|---|---|---|---|
| 1.001 | 2-Propyl | H | $CH_3$ | $OCH_3$ | $OCH_3$ | CH | 84–85 |
| 1.002 | t-Butyl | H | $CH_3$ | $OCH_3$ | $OCH_3$ | CH | 90–93 |
| 1.003 | 2-Butyl | H | $CH_3$ | $OCH_3$ | $OCH_3$ | CH | Öl |
| 1.004 | 2-Phenyl-2-propyl | H | $CH_2CH_3$ | $OCH_3$ | $OCH_3$ | CH | Öl |
| 1.005 | Cyclopentyl | H | $CH_3$ | $OCH_3$ | $OCH_3$ | CH | Öl |
| 1.006 | Cyclopentyl | H | $CH_2CH_3$ | $OCH_3$ | $OCH_3$ | CH | Ö 1 |

TABLE 1-continued

Thiocarboxylic acid derivatives of the formula I where Y is O and Z is S

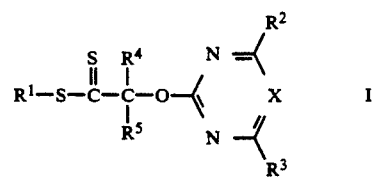

| Nr. | $R^4$ | $R^5$ | $R^1$ | $R^2$ | $R^3$ | X | Phys. Daten Fp [°C.] |
|---|---|---|---|---|---|---|---|
| 1.007 | 2-Propyl | H | $CH_3$ | $OCH_3$ | $OCH_2CH_2$ | | |
| 1.008 | t-Butyl | H | $CH_3$ | $OCH_3$ | $OCH_2CH_2$ | | |
| 1.009 | 2-Butyl | H | $CH_3$ | $OCH_3$ | $OCH_2CH_2$ | | |
| 1.010 | 2-Phenyl-2-propyl | H | $CH_3$ | $OCH_3$ | $OCH_2CH_2$ | | |
| 1.011 | Cyclopentyl | H | $CH_3$ | $OCH_3$ | $OCH_2CH_2$ | | |

The nitriles of the formula IV which are used as intermediates have the physical data and shown in Table 2.

TABLE 2

Nitriles of the formula IV

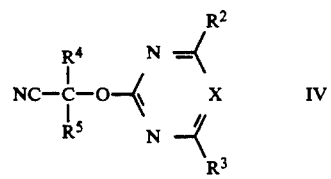

| Nr. | $R^4$ | $R^5$ | $R^2$ | $R^3$ | X | Phys. Daten Fp [°C.] |
|---|---|---|---|---|---|---|
| 2.001 | 2-Propyl | H | $OCH_3$ | $OCH_3$ | CH | Öl |
| 2.002 | t-Butyl | H | $OCH_3$ | $OCH_3$ | CH | 88–89 |
| 2.003 | 2-Butyl | H | $OCH_3$ | $OCH_3$ | CH | Öl |
| 2.004 | 2-Phenyl-2-propyl | H | $OCH_3$ | $OCH_3$ | CH | 91–93 |
| 2.005 | Cyclopentyl | H | $OCH_3$ | $OCH_3$ | CH | Öl |
| 2.006 | Methyl | H | $OCH_3$ | $OCH_3$ | CH | 97–98 |
| 2.007 | 2-Propyl | H | $OCH_3$ | $OCH_2CH_2$ | | |
| 2.008 | t-Butyl | H | $OCH_3$ | $OCH_2CH_2$ | | |
| 2.009 | 2-Butyl | H | $OCH_3$ | $OCH_2CH_2$ | | |
| 2.010 | 2-Phenyl-2-propyl | H | $OCH_3$ | $OCH_2CH_2$ | | |
| 2.011 | Cyclopentyl | H | $OCH_3$ | $OCH_2CH_2$ | | |
| 2.012 | 1-Phenyl-1-butyl | H | $OCH_3$ | $OCH_3$ | CH | 98–102 |
| 2.013 | 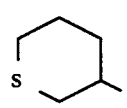 | H | $OCH_3$ | $OCH_3$ | CH | 58–63 |

Use Examples:

The herbicidal action of the compounds I could be demonstrated by means of greenhouse experiments:

The culture vessels used were plastic flower pots containing loamy sand with about 3% of humus as the substrate. The seeds of the test plants were sown separately according to species.

In the preemergence treatment, the active ingredients suspended or emulsified in water were applied directly after sowing by means of finely distributing nozzles. The pots were lightly watered in order to promote germination and growth and were then covered with transparent plastic covers until the plants had begun to grow. This covering ensures uniform germination of the test plants, unless this has been adversely affected by the active ingredients.

For the purpose of the postemergence treatment, the test plants were treated with the active ingredients suspended or emulsified in water only after they had reached a height of growth of from 3 to 15 cm, depending on the form of growth.

The plants were kept at 10°-25° C. or 20°-35° C., according to species. The test period extended over from 2 to 4 weeks. During this time, the plants were tended and their reaction to the individual treatments was evaluated.

Evaluation was based on a scale from 0 to 100. 100 means no emergence of the plants or complete destruction of at least the above-ground parts and 0 means no damage, or normal growth.

The plants used in the greenhouse experiments consist of the following species:

| Botanical name | Common name |
|---|---|
| Amaranthus retroflexus | Amaranth |
| Bromus spp. | Brome |
| Galium aparine | Catchweed |

When 3 kg/ha of a.i. is used in the postemergence method, undesirable broad-leaved plants and gramineous weeds can be very readily controlled with Example 1.003.

At an application rate of 0.5 kg/ha of active ingredient in the postemergence method, the compound 1.005 exhibits very good activity against the undesirable plants Chenopodium album, Galium aparine and Polygonum persicaria, high selectivity with respect to the crops cotton and rice being observed.

To determine the growth-regulating property of the test substances, test plants were grown on culture substrate adequately provided with nutrients, in plastic pots having a diameter of about 8 cm and a volume of about 300 ml.

In the postemergence method, the substances to be tested were sprayed in the form of an aqueous formulation onto the plants. The observed growth-regulating effect was demonstrated by measuring the height of growth at the end of the experiment. The measured values thus obtained were expressed as a ratio of the height of growth of the untreated plants. The comparative substance used was 2-chloroethyltrimethylammonium chloride (CCC).

The individual data are shown in Table 3, the concentration being stated in kg of active ingredient per hectare (kg/ha of a.i.).

TABLE 3

Bioregulatory effect of thiocarboxylic acid derivatives I when applied by the postemergence method

| Example No. | Application rate kg/ha a.i. | Relative height of growth Summer wheat a) | Summer barley b) |
|---|---|---|---|
| untreated | — | 100 | 100 |
| CCC | 3 | 85 | 103 |
| 1.001 | 0.06 | 67 | 73 |
| 1.003 | 0.025 | 70 | 73 |
| 1.004 | 0.025 | 67 | 73 |

TABLE 3-continued

Bioregulatory effect of thiocarboxylic acid derivatives I when applied by the postemergence method

| Example No. | Application rate kg/ha a.i. | Relative height of growth Summer wheat a) | Summer barley b) |
|---|---|---|---|
| 1.002 | 0.05 | 74 | 88 | a) "Star" variety
b) "Alexis" variety

We claim:
1. A thiocarboxylic acid of the formula I

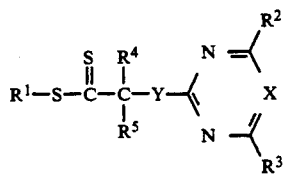

where
$R^1$ is $C_1$-$C_{10}$-alkyl which may carry from one to five halogen atoms or one of the following radicals: $C_1$-$C_4$-alkoxy, $C_1$-$C_4$-alkylthio, cyano, $C_1$-$C_8$-alkylcarbonyl, $C_1$-$C_8$-alkoxycarbonyl, $C_3$-$C_{12}$-cycloalkyl, phenyl, phenoxy or phenylcarbonyl, where the phenyl radicals in turn may carry from one to five halogen atoms and from one to three of the following radicals: $C_1$-$C_4$-alkyl, $C_1$-$C_4$-haloalkyl, $C_1$-$C_4$-alkoxy, $C_1$-$C_4$-haloalkoxy or $C_1$-$C_4$-alkylthio;

$C_1$-$C_{10}$-alkyl which may carry from one to five halogen atoms and carries one of the following radicals: a five-membered heteroaromatic structure selected from the group consisting of furtyl, thienyl, pyrryl, pyrazolyl, imidazolyl, triazolyl, isoxazolyl, oxazolyl, isothiazolyl, thiazolyl or thiadiazolyl, which may carry from one to four halogen atoms or one or two of the following radicals:

$C_1$-$C_4$-alkyl, $C_1$-$C_4$-haloalkyl, $C_1$-$C_4$-alkoxy, $C_1$14 $C_4$-haloalkoxy or $C_1$-$C_4$-alkylthio;

$C_2$-$C_6$-alkyl which carries one of the following radicals in the 2-position: $C_1$-$C_6$-alkoximino, $C_3$-$C_6$-alkenyloximino, $C_3$-$C_6$-haloalkenyloximino or benzyloximino;

$C_3$-$C_{12}$-cycloalkyl or $C_3$-$C_{12}$-cycloalkenyl which may carry from one to five halogen atoms or one of the following radicals: $C_1$-$C_4$-alkyl, $C_1$-$C_4$-alkoxy, $C_1$-$C_4$-alkylthio, cyano, $C_1$-$C_8$-alkylcarbonyl, $C_1$-$C_8$-alkoxycarbonyl, phenyl, phenoxy or phenylcarbonyl, where the phenyl radicals in turn may carry from one to five halogen atoms or from one to three of the following radicals: $C_1$-$C_4$-alkyl, $C_1$-$C_4$-haloalkyl, $C_1$-$C_4$-alkoxy, $C_1$-$C_4$-haloalkoxy or $C_1$-$C_4$-alkylthio;

$C_3$-$C_6$-alkenyl or $C_3$-$C_6$-alkynyl which may carry from one to five halogen atoms or one of the following radicals: $C_1$-$C_4$-alkoxy, $C_1$-$C_4$-alkylthio, cyano, $C_1$-$C_8$-alkylcarbonyl, $C_1$-$C_8$-alkoxycarbonyl, phenyl, phenoxy or phenylcarbonyl, where the phenyl radicals in turn may carry from one to five halogen atoms or from one to three of the following radicals: $C_1$-$C_4$-alkyl, $C_1$-$C_4$-haloalkyl, $C_1$-$C_4$-alkoxy, $C_1$-$C_4$-haloalkoxy or $C_1$-$C_4$-alkylthio;

phenyl which is unsubstituted or monosubstituted to trisubstituted by $C_1$-$C_4$-alkyl or $C_1$-$C_4$-alkoxy or monosubstituted to pentasubstituted by halogen;

$R^2$ is halogen, $C_1$–$C_4$-alkyl, $C_1$–$_4$-alkoxy, $C_1$–$C_4$-haloalkoxy or $C_1$–$C_4$-alkylthio;

X is $CR^6$, where $R^6$ is hydrogen or, together with $R^3$ forms a 3-membered or 4-membered alkylene or alkenylene chain, in each of which a methylene group is replaced with oxygen and each of which may be substituted by $C_1$–$C_4$alkyl, phenyl, alkoxy or $C_1$–$C_4$-alkoxycarbonyl;

$R^3$ is halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio or $R^3$ is bonded to $R^6$ as stated above to form a 5-membered or 6-membered ring;

$R^4$ is cyclopentyl;

$R^5$ is hydrogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, and Y is oxygen or sulfur.

2. A herbicidal composition which comprises a herbicidally effective amount of a thiocarboxylic acid derivative of the formula I as defined in claim 1 and conventional inert additives.

3. A method for controlling undesirable plant growth, wherein the undesirable plants or their habitat are or is treated with a herbicidal amount of a thiocarboxylic acid derivative of the formula I as defined in claim 1.

4. A plant growth regulating composition which comprises an effective amount of a thiocarboxylic acid derivative of the formula I as defined in claim 1 and conventional inert additives.

5. A method for regulating plant growth, wherein a bioregulatory amount of a thiocarboxylic acid derivative of the formula I as defined in claim 1 is allowed to act on the seeds, the plants or their habitat.

6. A thiocarboxylic acid derivative of the formula I as defined in claim 1, wherein $R^1$ is methyl, $R^2$ and $R^3$ are each methoxy, $R^4$ is cyclopentyl, $R^5$ is hydrogen, Y is oxygen and X is CH.

7. A herbicidal composition which comprises a herbicidally effective amount of a thiocarboxylic acid derivative of the formula I as defined in claim 6, and conventional inert additives.

8. A method for controlling undesirable plant growth, wherein the undesirable plants or their habitat are or is treated with a herbicidal amount of a thiocarboxylic acid derivative of the formula I as defined in claim 6.

9. A method for regulating plant growth, wherein a bioregulatory amount of a thiocarboxylic acid derivative of the formula I as defined in claim 6 is allowed to act on the seeds, the plants or their habitat.

* * * * *

UNITED STATES PATENT AND TRADEMARK OFFICE
CERTIFICATE OF CORRECTION

PATENT NO.: 5,318,945

DATED: June 7, 1994

INVENTOR(S): BAUMANN et al.

It is certified that error appears in the above-identified patent and that said Letters Patent is hereby corrected as shown below:

Column 28, claim 1, line 36, "furtyl" should be --furyl--.

Column 29, claim 1, line 1, after "$C_1$-$C_4$-alkyl" should be --$C_1$-$C_4$-haloalkyl--.

Column 29, claim 1, line 7, "$C_1$-$C_4$alkyl" should be --$C_1$-$C_4$-alkyl--.

Signed and Sealed this

Fourth Day of October, 1994

Attest:

BRUCE LEHMAN

Attesting Officer

Commissioner of Patents and Trademarks